(12) United States Patent
Porcs-Makkay et al.

(10) Patent No.: US 9,169,265 B2
(45) Date of Patent: Oct. 27, 2015

(54) PROCESS FOR PREPARING PHARMACEUTICAL COMPOUNDS AND INTERMEDIATE COMPOUNDS

(75) Inventors: Márta Porcs-Makkay, Pomáz (HU); Balázs Volk, Budapest (HU); Tamás Gregor, Csömör (HU); József Barkóczy, Budapest (HU); Tibor Mezei, Budapest (HU); Judit Broda, Budapest (HU); Bálint Nyulasi, Pápa (HU); György Ruzsics, Budapest (HU); Enikö Molnár, Érd (HU); József Debreczeni, Budapest (HU); Kálmán Nagy, Budapest (HU); Angéla Pandur, Mende (HU); Zsuzsanna Szent-Királlyi, Budapest (HU)

(73) Assignee: EGIS GYOGYSZERGYAR NYILVANOSAN MUKODO RESZVENYTARSASAG, Budapest (HU)

( * ) Notice: Subject to any disclaimer, the term of this patent is extended or adjusted under 35 U.S.C. 154(b) by 418 days.

(21) Appl. No.: 13/517,397

(22) PCT Filed: Dec. 21, 2010

(86) PCT No.: PCT/HU2010/000149
§ 371 (c)(1),
(2), (4) Date: Sep. 5, 2012

(87) PCT Pub. No.: WO2011/077174
PCT Pub. Date: Jun. 30, 2011

(65) Prior Publication Data
US 2012/0330018 A1    Dec. 27, 2012

(30) Foreign Application Priority Data
Dec. 21, 2009    (HU) ..................... 0900794

(51) Int. Cl.
*C07D 495/04*    (2006.01)
(52) U.S. Cl.
CPC .................. *C07D 495/04* (2013.01)

(58) Field of Classification Search
CPC combination set(s) only.
See application file for complete search history.

(56) References Cited

U.S. PATENT DOCUMENTS

| | | | |
|---|---|---|---|
| 4,740,510 A | 4/1988 | Badore et al. | |
| 5,288,726 A | 2/1994 | Koike et al. | |
| 5,874,581 A | 2/1999 | Ataka et al. | |

FOREIGN PATENT DOCUMENTS

| | | | |
|---|---|---|---|
| CN | 101177430 A | 5/2008 | |
| CN | 101245072 A | 8/2008 | |
| CN | 101245073 A | 8/2008 | |
| CN | 101250192 A | 8/2008 | |
| CN | 101250193 A | 8/2008 | |
| EP | 0 192 535 A1 | 8/1986 | |
| EP | 1 098 132 A1 | 5/2001 | |
| EP | 2 003 136 A1 | 12/2008 | |
| FR | 2 576 901 A1 | 8/1986 | |
| HU | 193625 B | 11/1987 | |
| WO | WO 96/11203 A1 | 4/1996 | |
| WO | WO 2007/115305 A2 | 10/2007 | |
| WO | WO 2008/108291 A1 | 12/2008 | |
| WO | WO 2009/006859 A2 | 1/2009 | |
| WO | WO 2009/062044 A2 | 5/2009 | |
| WO | WO 2009/066326 A2 | 5/2009 | |

OTHER PUBLICATIONS

Ronelle Russell; One-Pot Synthesis Aids Scale-Up and Data Collection; Pharmaceutical Technology, Advanstar Communications, Inc. US; Nov. 1, 2003; pp. 17-22.

*Primary Examiner* — David K O Dell
(74) *Attorney, Agent, or Firm* — Birch, Stewart, Kolasch & Birch, LLP

(57) ABSTRACT

The object of the present invention is a process for preparing the 2-acetoxi-5-(2-fluor-α-cyclopropyl-carbonyl-benzyl)-4,5,6,7-tetrahydro-4H-thieno[3,2-c]pyridine (prasugrel) of the formula (I). The process starts from crystalline 5-trityl-4,5,6,7-tetrahydro-thieno[3,2-c]pyridine of the formula (VI).
Further objects of the present invention are two novel crystalline forms of 5-trityl-4,5,6,7-tetrahydro-thieno[3,2-c]pyridine of the formula (VI) and the use thereof for preparing the compound of the formula (V) and process preparing thereof.

28 Claims, 3 Drawing Sheets

PROCESS FOR PREPARING PHARMACEUTICAL COMPOUNDS AND INTERMEDIATE COMPOUNDS

THE FIELD OF THE INVENTION

The present invention relates to a process for preparing 2-acetoxy-5-(2-fluoro-α-cyclopropyl-carbonyl-benzyl)-4,5,6,7-tetrahydro-4H-thieno[3,2-c]pyridine (prasugrel) of the formula

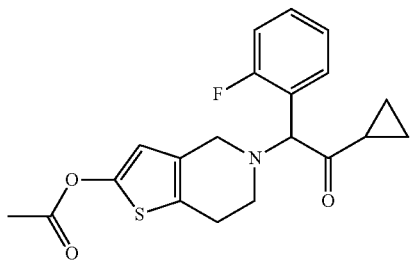

I which is advantageously and safely applicable on industrial scale. The present invention further relates to improved processes for the individual steps of the synthetic route and the crystalline polymorphs of the intermediate compound of the formula

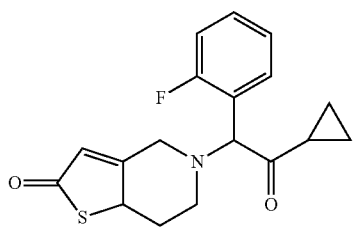

IV 2-acetoxy-5-(2-fluoro-α-cyclopropyl-carbonyl-benzyl)-4,5,6,7-tetrahydro-4H-thieno[3,2-c]pyridine (prasugrel) of formula (I) is an important representative of the tetrahydrothienopyridine derivatives which are used in the pharmaceutical industry as thrombocyte aggregation inhibitors.

THE STATE OF THE ART

The known synthetic routes for the preparation of prasugrel of the formula (I):

Prasugrel and the analogous compounds and a process for preparing thereof were first described in U.S. Pat. No. 5,288,726 B1. The preparation process according to U.S. Pat. No. 5,288,726 B1 is shown in reaction scheme 1.

Reaction scheme 1

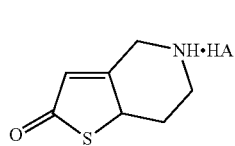 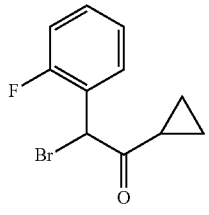
II III

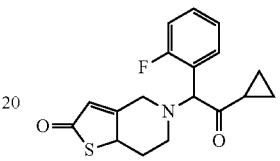 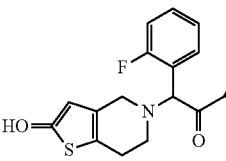
IV IVa

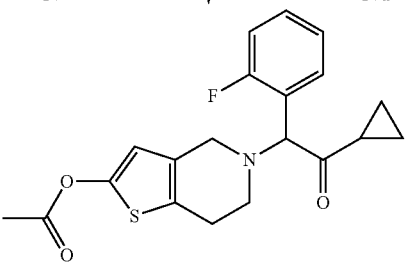

I

The 5,6,7,7a-tetrahydro-4H-thieno[3,2-c]pyridine-2-on hydrochloride of the formula

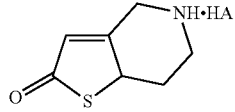

II

—wherein HA stands for HCl—is reacted with 2-bromo-1-cyclopropyl-2-(2-fluorophenyl)-ethanon of the formula

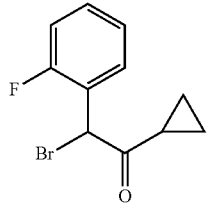

III in dimethyle-formamide at room temperature for 5 hours in the presence of anhydrous potassium carbonate (molar ratio: 1.0:1.0:2.2). The crude product is purified by column chromatography, the yield is 32%. The product is the brown and oily 5-[2-cyclopropyl-1-(2-fluorophenyl)-2-oxoethyl]-5,6,7,7a-tetrahydro-4H-thieno[3,2-c]pyridine-2-on of the formula (IV) mixed with the corresponding 2-hydroxy tautomer. The oily product is crystallized from diisopropyl ether and the yield is not disclosed. As the last step of the synthesis sodium hydride is added to the mixture of the formula (IV) and the solution of dimethyl-formamide and acetic anhydride. The reaction mixture is stirred for 3 hours at room temperature before processing. The crude product is purified by column chromatography. After evaporation the oily product is crystallized form diisopropyl ether, the process yields 65% of prasugrel base, calculated on the intermediate compound of formula (IV) and is very low, 21% calculated on the compound of formula (II)

The preparation of the starting material of the 5,6,7,7a-tetrahydro-4H-thieno[3,2-c]pyridine-2-on hydrochloride of the formula (II)—wherein HA stands for HCl—is not specified in U.S. Pat. No. 5,288,726 B1, the description only cites known processes without any details. The cited documents (M. Podesta et al., Eur. J. Med. Chem.—Chim. Ther. 9 (5), 487-490 (1974); and Japanese Patent Kokai Application No. Sho 61-246186) do not disclose any preparation process of the key intermediate compound of formula (II) (HA=Cl). Several further applications cite the synthetic route according to reaction scheme 2.

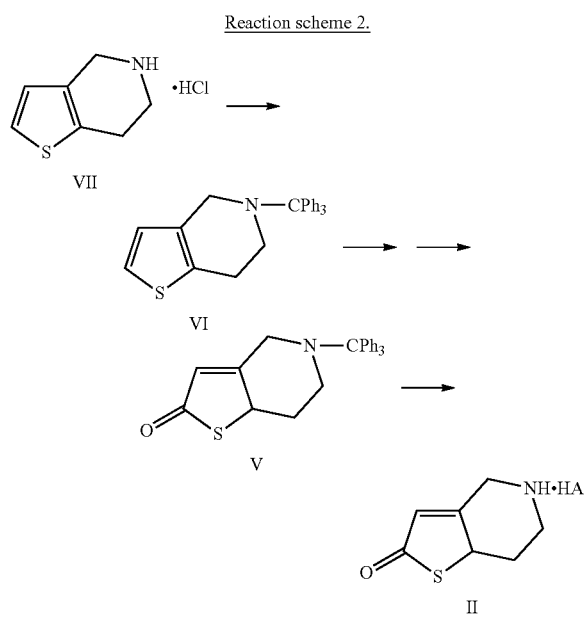

The disadvantage of the process disclosed by U.S. Pat. No. 5,288,726 B1 is that the compound of the formula (IV) and prasugrel of the formula (I) are obtained from the reaction mixture by column chromatography. It is known that column chromatography requires high amount of solvent, therefore scaling up is difficult and in the present case results in a low yield. Another disadvantage of the above process is using sodium-hydride by the acylation step of the preparation of the end-product. The use of sodium-hydride on industrial processes is dangerous and should comply with strict safety prescriptions. A further disadvantage of using sodium-hydride is the processing of paraffin which is used by suspending step.

The process which is disclosed in EP 1 098 132 B1 is similar to the process described in the basic patent. The 5,6,7,7a-tetrahydro-4H-thieno[3,2-c]pyridine-2-on hydrochloride of the formula (II) (HA=HCl) is reacted with 2-bromo-1-cyclopropyl-2-(2-fluorphenyl)-ethanon of the Formula (III) in dimethyl formamide at room temperature, but differently from the basic patent potassium hydrogen carbonate is used as a base and also a different molar ratio (1.0:0.93:2.8) is used. The reaction mixture is stirred for 2 hours at room temperature, the product is distributed between water and ethyl acetate and after evaporation the product is purified by chromatography. It is crystallized from diisopropyl ether. Thus the yield of intermediate compound of the Formula (IV) is 35%. Acetylation is similar to that described in the basic patent but a mixture of toluene and ethyl acetate in a ratio of 3 to 1 is used instead of 100 to 3 by chromatography as eluent. The yield of the last step is also 65% and the yield of the two steps together is only 23%.

In WO2007/115305 A1 a basically identical process to that according to the basic patent is described. The disclosed processes are based on the same disadvantageous steps as the basic patent and result in similarly low yields.

According to the process described in U.S. Pat. No. 5,874,581 B1 prasugrel of the Formula (I) is produced starting from 5,6,7,7a-tetrahydro-4H-thieno[3,2-c]pyridine-2-on toluene-4-sulfonate of Formula (II) (HA=p-toluene sulphonate, PTSA), wherein the carbonyl group in position 2 is silylated, and the protected intermediate compound of the formula

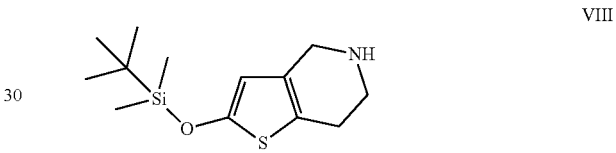

is linked with an appropriate ketone halogenide and the removal of protective group and O-acetylation of the in situ formed oxo intermediate compound of the formula (IV) are carried out in one step. The process is shown in the reaction scheme 3.

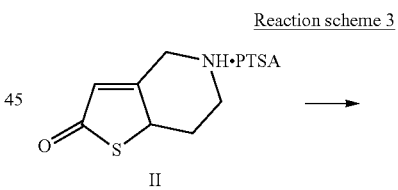

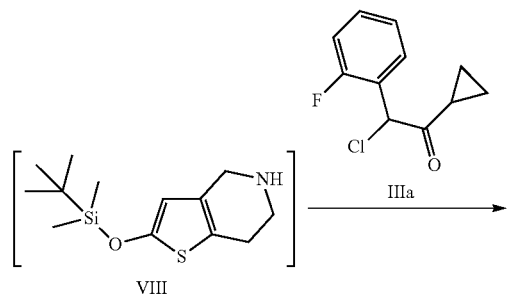

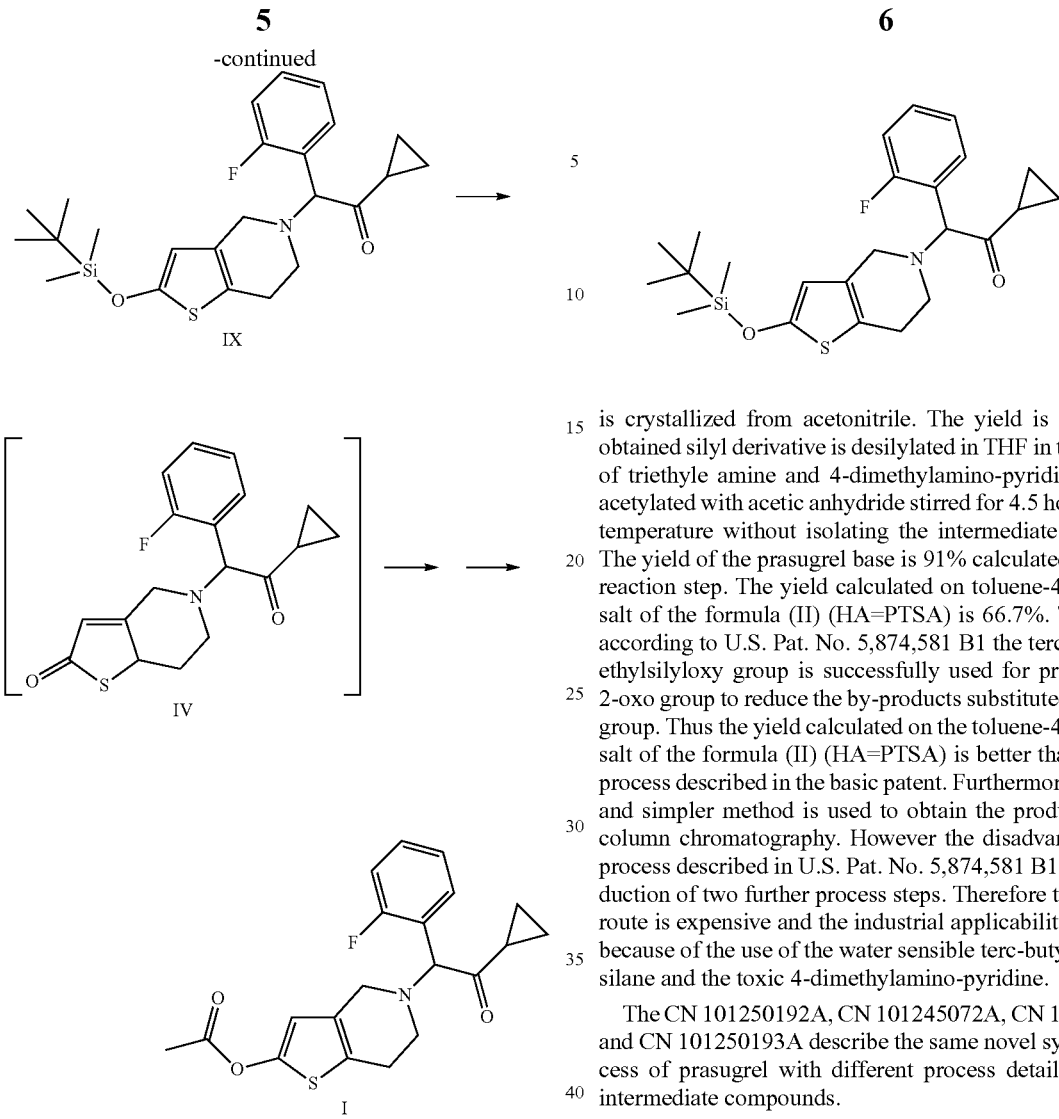

The detailed process is the following: The toluene-4-sulphonate salt of the formula (II) is reacted with terc-butyl-dimethyl-chlorosilane in the presence of triethyl amine in dichloro methane solvent for 3 hours at room temperature and the 2-(terc-butyl-dimethylsilyloxy)-4,5,6,7-tetrahydrothieno[3,2-c]pyridine toluene-4-sulfonate is formed. The formed compound is further reacted with 2-chloro-1-cyclopropyl-2-(2-fluorophenyl)-ethanon of the formula

without isolation in the presence of sodium iodide, by adding further triethyl amine, at 45° C. and stirred for 12 hours. After processing the reaction mixture the 2-(terc-butyl-dimethylsilyloxy)-5-(α-cyclopropylcarbonile-2-fluorobenzyl)-4,5,6,7-tetrahydrothieno[3,2-c]pyridine of the formula is crystallized from acetonitrile. The yield is 73.3%. The obtained silyl derivative is desilylated in THF in the presence of triethyle amine and 4-dimethylamino-pyridine and it is acetylated with acetic anhydride stirred for 4.5 hours at room temperature without isolating the intermediate compound. The yield of the prasugrel base is 91% calculated on the last reaction step. The yield calculated on toluene-4-sulphonate salt of the formula (II) (HA=PTSA) is 66.7%. The process according to U.S. Pat. No. 5,874,581 B1 the terc-butyl-dimethylsilyloxy group is successfully used for protecting the 2-oxo group to reduce the by-products substituted on the oxo group. Thus the yield calculated on the toluene-4-sulphonate salt of the formula (II) (HA=PTSA) is better than using the process described in the basic patent. Furthermore preferable and simpler method is used to obtain the product than the column chromatography. However the disadvantage of the process described in U.S. Pat. No. 5,874,581 B1 is the introduction of two further process steps. Therefore the synthetic route is expensive and the industrial applicability is difficult because of the use of the water sensible terc-butyl-dimethylsilane and the toxic 4-dimethylamino-pyridine.

The CN 101250192A, CN 101245072A, CN 101245073A and CN 101250193A describe the same novel synthetic process of prasugrel with different process details of certain intermediate compounds.

The CN 101250192A describes the preparation of the prasugrel base from the intermediate compound of the formula wherein the oxo-group is protected by akyl group. The process is shown on the reaction scheme 4.

Reaction scheme 4

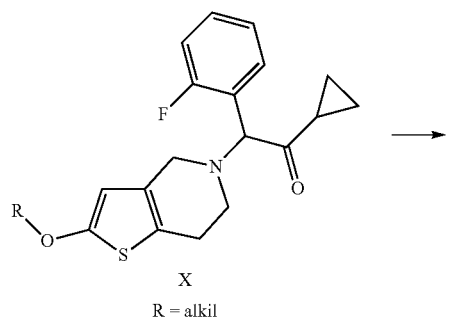

R = alkil

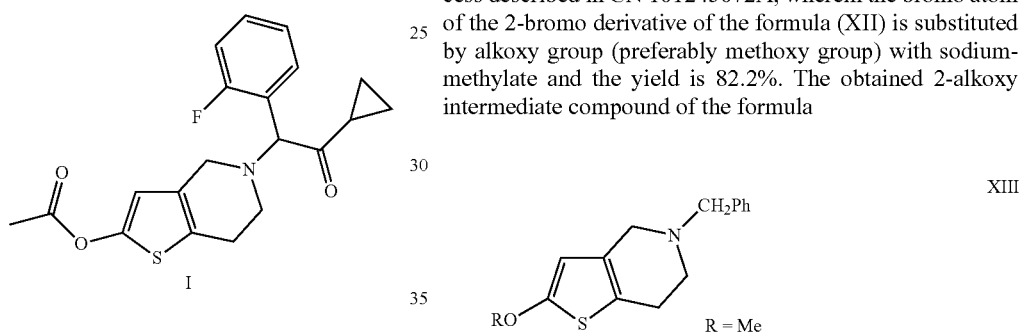

The protective group is removed by using acidic and mild reaction medium. The advantage of the process is that it does not use low temperature, flammable or explosive reagents and the process results high yield.

According to the CN 101245072A by benzylation of the 4,5,6,7-tetrahydro-thieno[3,2-c]pyridine of the formula VIIa the yield of the intermediate compound of the formula (XI) is 98.7%. The 2-bromo-N-benzyle intermediate compound of the formula

XII

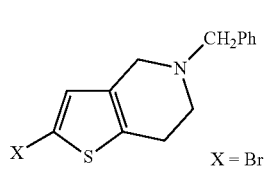

X = Br is obtained by bromination of the compound of the formula (IX) with the yield of 97.8% according to the reaction scheme 5.

Reaction scheme 5

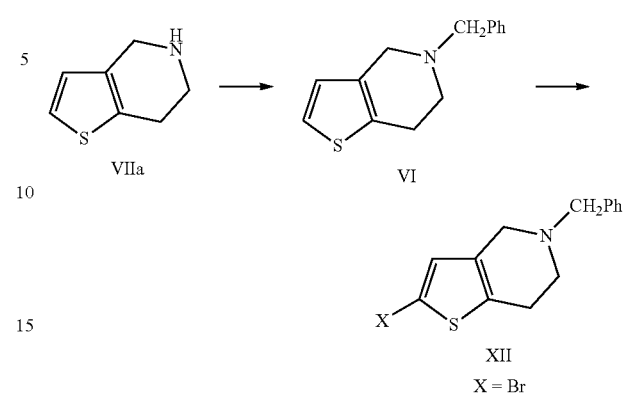

X = Br

The compound of the formula (XII) is converted to the prasugrel of the formula (I) in several further steps.

CN 101245073A discloses an improved variant of the process described in CN 101245072A, wherein the bromo atom of the 2-bromo derivative of the formula (XII) is substituted by alkoxy group (preferably methoxy group) with sodium-methylate and the yield is 82.2%. The obtained 2-alkoxy intermediate compound of the formula

XIII

R = Me is converted to the prasugrel of the formula (I) in several further steps according to the reaction scheme 6.

Reaction scheme 6

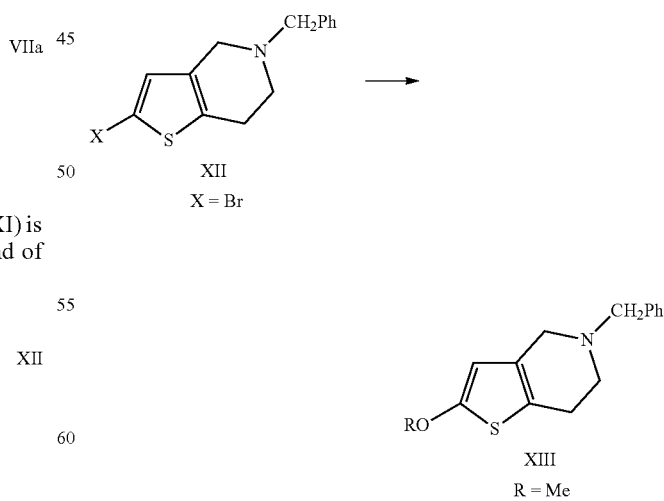

R = Me

In CN 101250193A the 2-alkoxy intermediate compound is formed by linking the 2-alkoxy-4,5,6,7-tetrahydro-thieno[3,2-c]pyridine of the formula

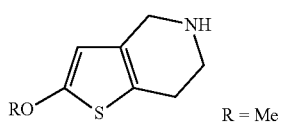

with 2-bromo-1-cyclopropyl-2-(2-fluorphenyl)-ethanone of the formula (III) in the presence of Cu(I) salt and iodine salt (reaction scheme 7.)

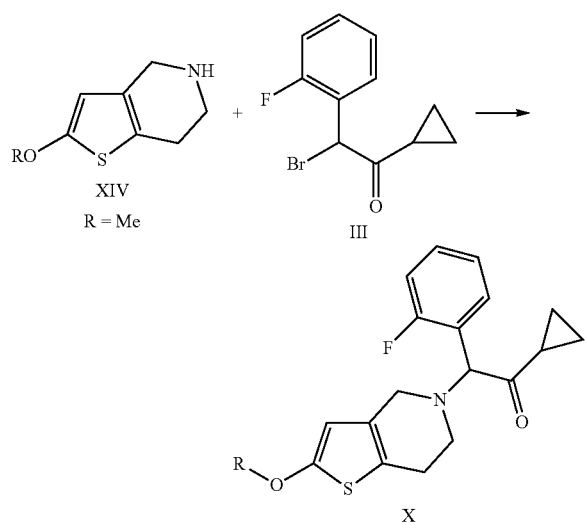

The advantage of the process is that they do not use low temperature, flammable or explosive reagents and the process results high yield The disadvantages of the processes described in CN 101250192A, CN 101245072A, CN 101245073A and CN 101250193A are that the economical processing of the dealkylation step of the alkoxy group (preferably demethylation of the methoxy group) is difficult. Further disadvantage is that while catalytic hydrogenation of the protective benzyl group on the nitrogen atom the formed thiophene compound is able to act as a catalytic poison.

WO2008/108291 discloses a process for the preparation of prasugrel hydrochloride consisting a decreased amount of the impurity of 3-chloro-propyl which is formed by ring opening while chlorination of the cyclopropyl ring of prasugrel. The 1-cyclopropyl-2-(2-fluorphenyl)-ethanone of the formula (XV)

XV

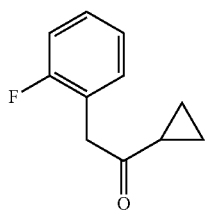

is chlorinated in position 2 at low temperature and the obtained intermediate compound of the formula (Ma) is linked with 5,6,7,7a-tetrahydro-4H-thieno[3,2-c]pyridine-2-on derivative of the formula (XIV, R=trialkyl-silyl) which is protected on the oxygen atom (reaction scheme 8.)

Reaction scheme 8

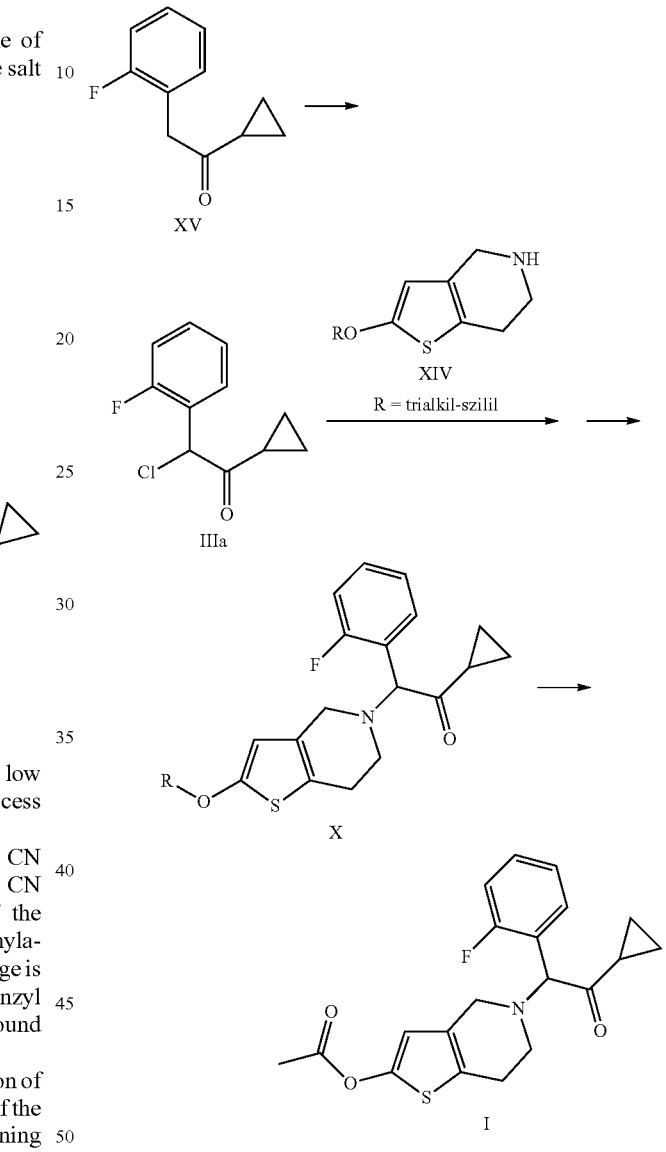

EP 2 003 136 A1 describes the process for preparing high purity prasugrel base and acid addition salts thereof (preferably hydrochloride), with reduced content of the deacetyl impurity of the formula (IV). The process disclosed in WO96/11203 is used for producing prasugrel to salt formation and purification of the base. 2-chloro-1-cyclopropyl-2-(2-fluorophenyl)-ethanon of the formula (Ma) is used by linking, which is formed by halogenation of the appropriate keton of the formula (XV) with chlorine gas, with the yield of 80%. The high purity prasugrel base is recrystallized. Several solvents preferably acetonitrile are mentioned for recrystallization. The synthetic routes and the intermediate compounds are known, which are used in the process. The disadvantage of the present process is using chlorine gas, which is poisonous, difficult to handle and destruction.

WO2009/006859 describes a process, wherein the 5,6,7,7a-tetrahydro-4H-thieno[3,2-c]pyridine-2-on salt of the formula (II) is linked with the appropriate 2-methoxy derivative of the formula

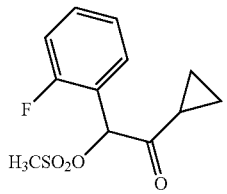

XVI instead of the 2-bromo-1-cyclopropyl-2-(2-fluorphenyl)-ethanon of the formula (III). After preparation of the intermediate compound of the formula (IV) with column chromatography, the yield is 23.7% according to one of the versions and 65.4% according to the other one. The intermediate compound of the formula (XVI) is prepared from 2-fluoro-benzaldehyde and trimethylsilyl-cyanide in several steps, using expensive reagents and the yield is 38.5%. The crude, oily compound of the formula (II) is obtained after acylation and subsequent column chromatography and the crystalline compound is obtained by crystallization from diethyl ether, wherein the yield is 29.2%. The process is not economical and the final product is obtained in each version by column chromatography. The description does not disclose any data about the impurity profile of the final product.

WO2009/062044 discloses two synthetic routes for preparing prasugrel. One of the routes yields 4.6% calculated on the 4,5,6,7-tetrahydro-thieno[3,2-c]pyridine hydrochloride of the formula (VII) or 3.7% considering also the recrystallization step by using the process described in the basic patent with little modification. The other route is shown in the reaction scheme 9.

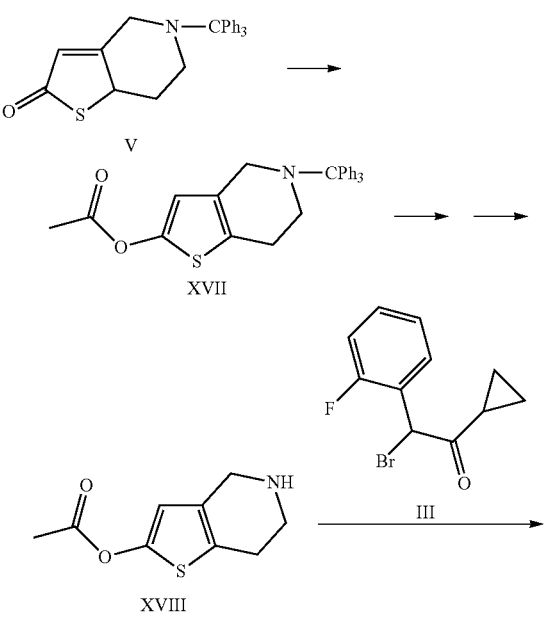

Reaction scheme 9

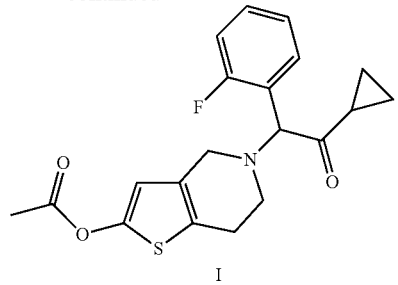

I

The 5-trityl-5,6,7,7a-tetrahydro-4H-thieno[3,2-c]pyridine-2-on of the formula

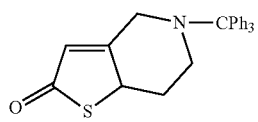

V is acetylated and the compound of the formula

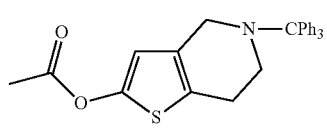

XVII is formed and the protecting group is removed form the nitrogen atom. The thus formed derivative of the formula

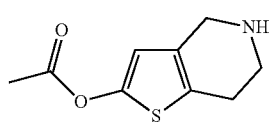

XVIII is then linked with the bromo-ketone of the formula (III). The yield is 4.1% calculated on the 4,5,6,7-tetrahydro-thieno[3,2-c]pyridine hydrochloride of the formula (VII) or 3.1% considering also the recrystallization step. It is lower than in the previous process variant.

WO2009/066326 describes an improved and up-scaled process of the basic patent. The 5,6,7,7a-tetrahydro-4H-thieno[3,2-c]pyridine-2-on salt of the formula (II) and the 2-bromo-1-cyclopropyl-2-(2-fluorphenyl)-ethanon of the formula (III) is linked in the presence of potassium carbonate. The formed compound of the formula (IV) is prepared in oily form and is acetylated in the presence of the acid binder diisopropyl-ethyl-amine (DIPEA). The highest yield calculated on the 4,5,6,7-tetrahydro-thieno[3,2-c]pyridine hydrochloride of the formula (VII) is 19.3 and 13%, if we consider the final purification step. Further disadvantages of the process are the use of two different bases in two steps and isolation of the intermediate compound of the formula (VII) is unnecessary, thus economizing manpower and solvent costs.

The Prior Art of the Early Steps of the Synthetic Route

The preparation of the 5-trityl-4,5,6,7-tetrahydro-thieno[3,2-c]pyridine of the formula (VI) was first described in FR 2

576 901 B1. The yield is 96% and the 4,5,6,7-tetrahydro-thieno[3,2-c]pyridine of the formula (VIIa) is reacted with trityl-chloride in the presence of triethyle amine, in dichloro methane medium, at room temperature for 20 hours. The reaction mixture is mixed then with water. After separating the phases the organic layer is dried, evaporated and filtered with dichloro methane on silica gel bed. Paste-like compound of the formula (VI)

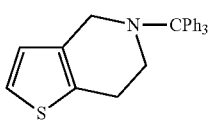

VI is obtained, which has a melting point 95° C. The quality of the product is not disclosed. Although the yield of the product is high the process is rather unsuitable for industrial application, because the halogenated solvent reaction medium furthermore the quality of product is not defined. This might be the explanation of the 64% yield of the next step, wherein the compound of the formula (VI) is converted to the 4,5,6,7-tetrahydro-thieno[3,2-c]pyridine of the formula (V)

In WO2009/062044 the process starts from the 4,5,6,7-tetrahydro-thieno[3,2-c]pyridine hydrochloride of the formula (VII). The base is liberated form the hydrochloride in dichloro methane with ammonium-hydroxide. The base is tritylated in dichloro methane in the presence of triethyl amine stirring for 1 hour at room temperature. The yield of the trityl intermediate compound is 74.8% and the purity of the product is 89.16 measured by HPLC.

In WO2009/066326 the process starts from the 4,5,6,7-tetrahydro-thieno[3,2-c]pyridine of the formula (VIIa). The compound of the formula (VII) is tritylated in dichloro methane in the presence of triethyl amine stirred for 16 hours at 0-5° C. The compound of the formula (VI) is filtered form cyclohexane with the yield of 87.5%.

In US2009/066326 the process starts from the 4,5,6,7-tetrahydro-thieno[3,2-c]pyridine of the formula (VIIa), but the reaction conditions used are different. The free base is converted to the yellow-brown, solid 5-trityl-4,5,6,7-tetrahydro-thieno[3,2-c]pyridine of the formula (VI) in the presence of sodium-hydride, with tritylchloride, in tetrahydrofurane medium, at 0° C., within one hour by flash chromatography. The product yields in 50%, and is characterized by $^1$H-NMR and mass spectrum. The process is fast, but the disadvantages are the following: the yield is low, sodium hydride is used as a base and the purification with flash chromatography is industrially not applicable.

Another process for preparing 5-trityl-4,5,6,7-tetrahydro-thieno[3,2-c]pyridine of the formula (VI) is described in A J. Am. Chem. Soc. 2007, 10, 2768, wherein the compound of the formula (VI) is converted to the 5-trityl-2,4,5,6,7,7a-hexahydro-thieno[3,2-c]pyridine of the formula

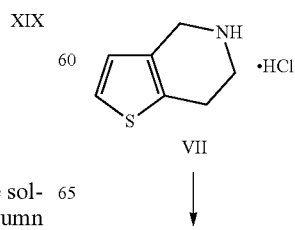

XIX by oxidation with sulfuryl chloride in dichloro methane solvent at 0° C. The remaining product is purified by column chromatography; the yellow, solid compound of the formula (VI) has the melting point of 85-87° C. and the process yields 66%. The disadvantage of the process is that the starting compound is difficulty available; the column chromatography used for scale-up is expensive and limited. The synthetic route is shown on the reaction scheme 10.

Reaction scheme 10

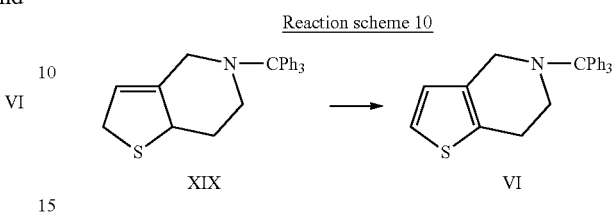

XIX      VI

The FR 2 576 901 B1 discloses the preparation of the -trityl-5,6,7,7a-tetrahydro-4H-thieno[3,2-c]pyridine-2-on of the formula (V) from the trityl derivative of the formula (VI), and it discloses the further preparation of the 5,6,7,7a-tetrahydro-4H-thieno[3,2-c]pyridine-2-on hydrochloride of the formula (II), (wherein HA=HCl) starting form the compound of the formula (V). The 5-trityl-4,5,6,7-tetrahydro-thieno[3,2-c]pyridine of the formula (VI) is reacted with butyl lithium, tributyl borate and hydrogen peroxide in tetrahydrofuraneous medium. The reaction mixture is processed and the formed oily product is recrystallised with diisopropyl ether. The yield is 64% of the compound of the formula (V). The trityl protecting group is removed from the intermediate compound of the formula (V) by boiling with 98 w/w % formic acid at 90° C. for 1 hour. After processing the reaction mixture the yield of the 5,6,7,7a-tetrahydro-4H-thieno[3,2-c]pyridine-2-on hydrochloride of the formula (II), (wherein HA=HCl) is 81% calculated on the compound of the formula (V).

SUMMARY OF THE INVENTION

The aim of the present invention is to provide an economic, simple synthetic route, which does not require column chromatography, is applicable on industrial scale and provides high yield, starts from the 4,5,6,7-tetrahydro-thieno[3,2-c] pyridine hydrochloride of the formula (VII) and provides the prasugrel of the formula (I).

The above aim is solved by the process of the present invention.

The object of the present invention is a process for preparing the 2-acetoxi-5-(2-fluor-α-cyclopropyl-carbonyl-benzyl)-4,5,6,7-tetrahydro-4H-thieno[3,2-c]pyridine (prasugrel) of the formula (I). The process starts form crystalline 5-trityl-4,5,6,7-tetrahydro-thieno[3,2-c]pyridine of the formula (VI).

Reaction scheme 11:
Preparation process of prasugrel according to the present invention

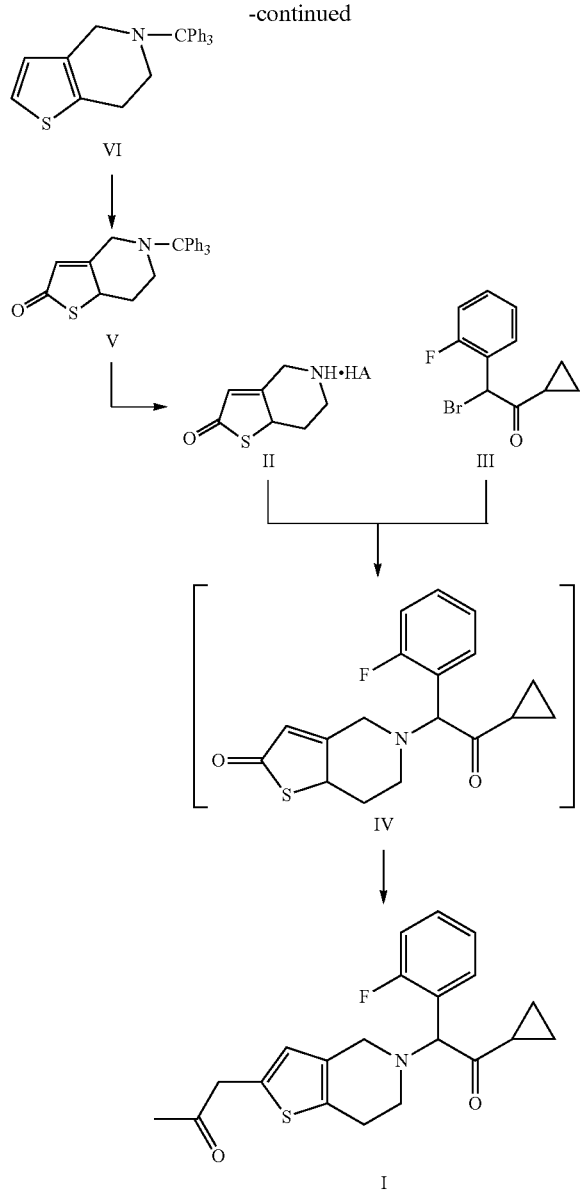

The present invention further relates to a the process for preparing 5-trityl-4,5,6,7-tetrahydro-thieno[3,2-c]pyridine of the formula (VI) starting from 4,5,6,7-tetrahydro-thieno[3,2-c]pyridine hydrochloride of the formula (VII)

Further objects of the present invention are two novel crystalline forms of 5-trityl-4,5,6,7-tetrahydro-thieno[3,2-c]pyridine of the formula (VI) and the use thereof for preparing the compound of the formula (V).

The invention further relates to an improved process for preparing 5-trityl-5,6,7,7a-tetrahydro-4H-thieno[3,2-c]pyridine-2-on of the formula (V) starting from the novel crystalline Form I of the 5-trityl-4,5,6,7-tetrahydro-thieno[3,2-c]pyridine of the formula (VI).

The invention further relates to an improved process for preparing 5,6,7,7a-tetrahydro-4H-thieno[3,2-c]pyridine-2-on of the formula (II) starting from the 5-trityl-5,6,7,7a-tetrahydro-4H-thieno[3,2-c]pyridine-2-on of the formula (V).

The invention further relates to an improved process for preparing the prasugrel of the formula (I) starting from the novel crystalline polymorph I of the 5-trityl-4,5,6,7-tetrahydro-thieno[3,2-c]pyridine of the formula (VI) using 5-trityl-5,6,7,7a-tetrahydro-4H-thieno[3,2-c]pyridine-2-on of the formula (V) and 5,6,7,7a-tetrahydro-4H-thieno[3,2-c]pyridine-2-on of the formula (II) as intermediate compounds.

The invention further relates to an improved process for preparing the prasugrel of the formula (I) starting from 4,5,6,7-tetrahydro-thieno[3,2-c]pyridine hydrochloride of the formula (VII) using the novel crystalline polymorph I of the 5-trityl-4,5,6,7-tetrahydro-thieno[3,2-c]pyridine of the formula (VI), the 5-trityl-5,6,7,7a-tetrahydro-4H-thieno[3,2-c]pyridine-2-on of the formula (V) and the 5,6,7,7a-tetrahydro-4H-thieno[3,2-c]pyridine-2-on of the formula (II) as intermediate compounds.

The invention further relates to an improved process for preparing the prasugrel of the formula (I) started from 4,5,6,7-tetrahydro-thieno[3,2-c]pyridine hydrochloride of the formula (VII) using the novel crystalline polymorph I of the 5-trityl-4,5,6,7-tetrahydro-thieno[3,2-c]pyridine of the formula (VI), and the 5,6,7,7a-tetrahydro-4H-thieno[3,2-c]pyridine-2-on of the formula (II) as intermediate compounds.

DETAILED DESCRIPTION OF THE INVENTION

The aim of the present invention is to provide an improved process, wherein the tritylation of the 4,5,6,7-tetrahydro-thieno[3,2-c]pyridine hydrochloride of the formula (VII) is carried out by a one-pot method, without isolating the 4,5,6,7-tetrahydro-thieno[3,2-c]pyridine of the formula (VIIa) in the presence of a base, which is suitable both for the liberation of the base from the hydrochloride salt of the formula (VII) and for binding the hydrochloride which is formed in the tritylation reaction.

The invention relates to an improved process for preparing 5-trityl-4,5,6,7-tetrahydro-thieno[3,2-c]pyridine of the formula (VI).

The starting compound of the process is 4,5,6,7-tetrahydro-thieno[3,2-c]pyridine hydrochloride of the formula (VII), which is converted into 5-trityl-4,5,6,7-tetrahydro-thieno[3,2-c]pyridine of the formula (VI) without isolating the 4,5,6,7-tetrahydro-thieno[3,2-c]pyridine of the formula (VIIa).

Our further aim was to provide a process, wherein the use of dichloro methane is not required, in contrast with the process according to FR 2 576 901 B1. It is known that the processes, which use halogenated solvents are not environmental friendly, therefore it is expedient to avoid the use thereof. One of the advantages of the present invention is that the dichloro methane is replaced by an other non-halogenated solvent.

It has been surprisingly found that the tritylation of the compound of the formula (VII) can be performed in other organic solvents, than dichloro methane. The suitable solvents are aromatic hydrocarbons (e.g. toluene), ether-type solvents (e.g. tetrahydrofurane/THF), dioxane, methyle-tercbutyl-ether, acidamide-type solvents (e.g. N, N-dimethylformamide/DMF, N,N-dimethylacetamide, N-methyle-pyrrolidone), nitrile-type solvents (e.g. acetonitrile), ketone-type solvents (e.g. methyle-ethyl-ketone). The reaction is performed in the presence of organic base. The organic base can be for example triethyl amine, N,N-diisopropyl-ethylamine, pyridine etc. The process of the present invention takes place in a surprisingly short time (10-15 minutes), while the reaction time of the process of FR 2 576 901 B1 is 20 hours. Solvents, from which the tritylated crystalline compound precipitates directly or after dilution the reaction mixture with water, are preferably used. Such solvents can be for example acetonitrile, DMF etc. Thus the tritylated product can be obtained by simple filtration. The time and work-consuming processing of the reaction mixture is not required and aqueous mother-lye does not formed. The product thus obtained can be used at the further synthetic steps without purification.

Further objects of the present invention are two novel polymorphs of the 5-trityl-4,5,6,7-tetrahydro-thieno[3,2-c]pyridine of the formula (VI).

Figure 1:
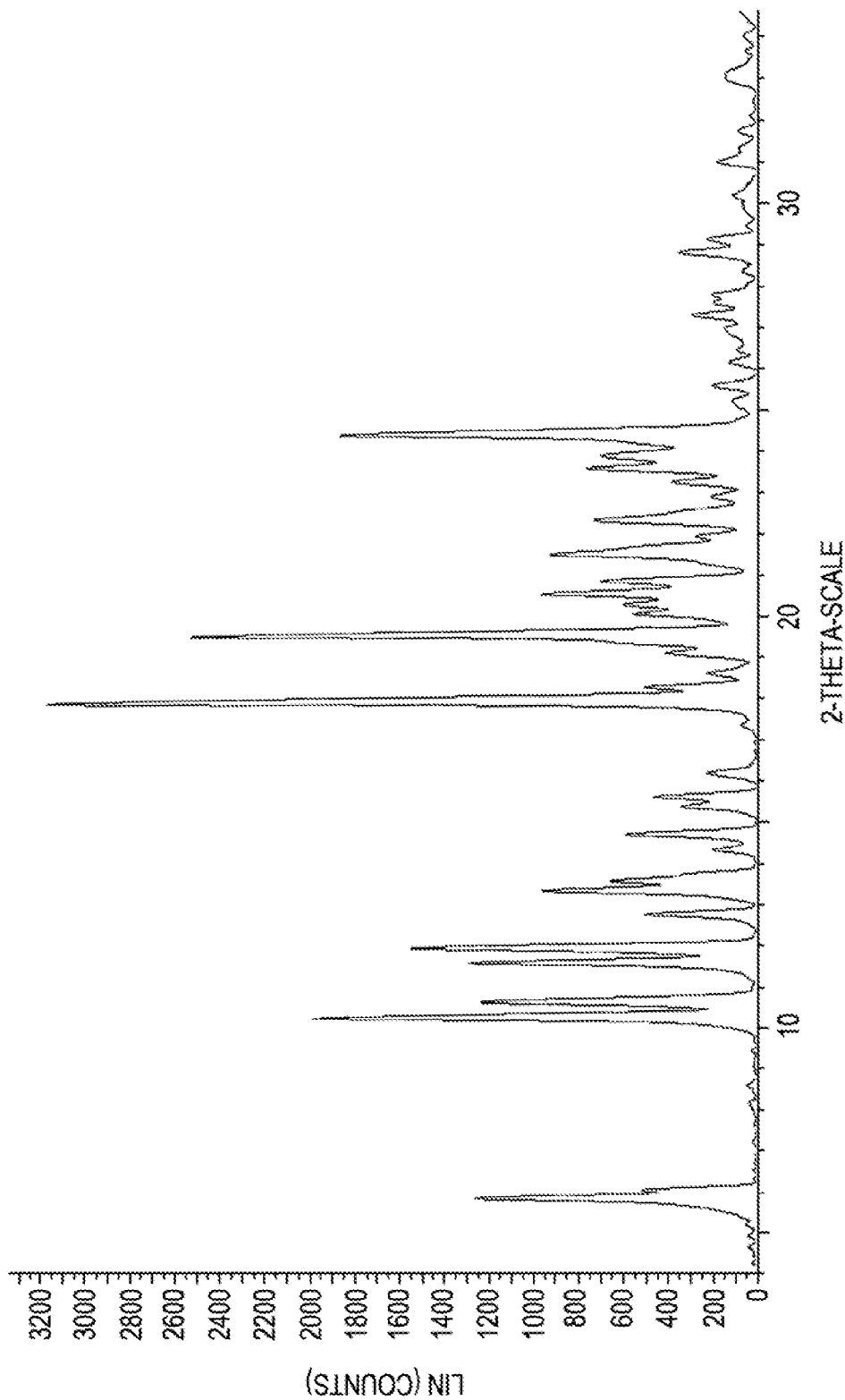
FIG. 1 depicts the X-ray powder diffraction pattern of Form I of 5-trityl-4,5,6,7-tetrahydro-thieno [3,2-c]pyridine of the formula (VI).

It has been surprisingly found that the obtained 5-trityl-4,5,6,7-tetrahydro-thieno[3,2-c]pyridine of the formula (VI) is in crystalline form with high melting point (169-170° C.) contrary to the previously known forms with law melting point (95° C.). The novel polymorph is the Form I and its X-ray powder diffraction pattern is shown in FIG. 1.

On carrying out the process disclosed in FR 2 576 901 B1, the known compound with 92-97° C. melting point is obtained by evaporating the reaction mixture containing dichloro methane. The X-ray powder diffraction pattern of the obtained compound is shown in the FIG. 2., the compound is amorphous and contains 5-25 mol % of dichloro methane. While storing for some months or drying in vacuo at 80° C., the amorphous compound converts into the polymorphic form, named Form II. The X-ray powder diffractogram of Form II is shown in FIG. 3. and has a melting point of 147-152° C.

In the pharmaceutical industry there is a serious demand for reproducible processes which resulted in pure and morphologically uniform active and intermediate compounds. The morphologically uniform product also has technical importance, because the single polymorphs show significantly different properties which influence the processing (solubility, drying and filtering). A further demand for the reproducible process which results in pure and morphologically uniform product is that the process should be economical and applicable on industrial scale.

The two crystalline 5-trityl-4,5,6,7-tetrahydro-thieno[3,2-c]pyridine forms of the formula (VI) of the present invention are obtained with high purity, do not contain any residual solvents, have advantageous physico-chemical properties and are more stable than the amorphous form of the formula (VI) which is known form prior art. The novel polymorphs of the formula (VI) are furthermore reproducible on industrial scale.

An object of the present invention is Form I of the 5-trityl-4,5,6,7-tetrahydro-thieno[3,2-c]pyridine of the formula (VI). Its X-ray powder diffraction pattern is shown in FIG. 1. and the characteristic X-ray powder diffraction pattern, position of the peaks (Form I) and relative intensity (>5%) are shown in table 1.

TABLE 1

| Peak No. | Angle 2-Theta ° | d value Angstrom | Intensity % |
| --- | --- | --- | --- |
| 1 | 5.790 | 15.25071 | 39.1 |
| 2 | 5.986 | 14.75396 | 16.2 |
| 3 | 10.236 | 8.63495 | 62.5 |
| 4 | 10.594 | 8.34411 | 39 |
| 5 | 11.553 | 7.65334 | 40.5 |
| 6 | 11.938 | 7.40748 | 48.7 |
| 7 | 12.718 | 6.95478 | 15.7 |
| 8 | 13.336 | 6.63384 | 30.2 |
| 9 | 13.543 | 6.53296 | 20.6 |
| 10 | 14.308 | 6.18523 | 6.1 |
| 11 | 14.685 | 6.02737 | 18.5 |
| 12 | 15.357 | 5.76519 | 10.8 |
| 13 | 15.555 | 5.69199 | 14.5 |
| 14 | 16.139 | 5.48733 | 7.1 |
| 15 | 17.929 | 4.94340 | 100 |
| 16 | 18.259 | 4.85488 | 16 |
| 17 | 18.598 | 4.76707 | 7 |
| 18 | 19.052 | 4.65440 | 13 |
| 19 | 19.527 | 4.54244 | 79.8 |
| 20 | 20.032 | 4.42890 | 16.9 |
| 21 | 20.254 | 4.38092 | 18.9 |
| 22 | 20.536 | 4.32133 | 30.4 |
| 23 | 20.853 | 4.25637 | 21.8 |
| 24 | 21.525 | 4.12511 | 29.1 |
| 25 | 21.907 | 4.05403 | 9.1 |
| 26 | 22.343 | 3.97587 | 22.8 |
| 27 | 22.894 | 3.88134 | 6.4 |
| 28 | 23.240 | 3.82430 | 11.9 |
| 29 | 23.593 | 3.76788 | 23.7 |
| 30 | 23.903 | 3.71978 | 21.7 |
| 31 | 24.427 | 3.64109 | 58.6 |
| 32 | 25.575 | 3.48021 | 6.2 |
| 33 | 27.268 | 3.26790 | 9.1 |
| 34 | 27.590 | 3.23049 | 6.6 |
| 35 | 27.791 | 3.20752 | 5.9 |
| 36 | 28.809 | 3.09645 | 10.8 |
| 37 | 29.107 | 3.06544 | 7.1 |
| 38 | 30.996 | 2.88284 | 5.9 |
| 39 | 33.051 | 2.70808 | 4.7 |

The measuring conditions of the powder X-ray crystallography were the following:

Apparatus: BRUKER D8 ADVANCE powder diffractometer

Radiation: CuK$\alpha_1$($\lambda$=1.54060 Å), CuK$\alpha_2$($\lambda$=1.54439 Å)

Voltage: 40 kV

Anode current: 30 mA

Accessories: Gobel-mirror, Soller-slit, sample changer, transmission position

Detector: LynxEye

Measurement was steady Θ/Θ scan: 4-35° 2Θ

Step size: 0.02°

Sample: non-powder, measured and stored at room temperature

The position of characteristic powder X-ray diffraction peaks of the Form I are the following: 2Θ(±0.2° 2Θ): 10,236; 11,938; 17,929; 19,527; 24,427.

Preferably the position of characteristic powder X-ray diffraction peaks of the Form I are the following: 2Θ(±0.2° 2Θ): 5,790; 10,236; 10,594; 11,553; 11,938; 13,336; 17,929; 19,527; 20,536; 24,427.

A further object of the present invention is Form II of the 5-trityl-4,5,6,7-tetrahydro-thieno[3,2-c]pyridine of the formula (VI). Its X-ray powder diffraction pattern is shown in FIG. 3. and the characteristic X-ray powder diffraction pattern, position of the peaks (Form II) and relative intensity (>5%) are shown in table 2.

TABLE 2

| Peak No. | Angle 2-Theta ° | d value Angstrom | Intensity % |
|---|---|---|---|
| 1 | 5.484 | 16.10115 | 6 |
| 2 | 9.139 | 9.66847 | 13.7 |
| 3 | 9.768 | 9.04746 | 35.8 |
| 4 | 10.059 | 8.78663 | 37.7 |
| 5 | 10.887 | 8.12012 | 100 |
| 6 | 11.614 | 7.61336 | 10.6 |
| 7 | 12.446 | 7.10628 | 5.5 |
| 8 | 14.015 | 6.31409 | 9.1 |
| 9 | 14.488 | 6.10889 | 15.9 |
| 10 | 14.675 | 6.03144 | 7.5 |
| 11 | 15.058 | 5.87888 | 5 |
| 12 | 15.317 | 5.77991 | 18.9 |
| 13 | 15.522 | 5.70431 | 11 |
| 14 | 15.864 | 5.58185 | 9 |
| 15 | 16.106 | 5.49856 | 9.8 |
| 16 | 16.810 | 5.26998 | 49.5 |
| 17 | 18.001 | 4.92381 | 49.8 |
| 18 | 18.357 | 4.82905 | 91 |
| 19 | 19.351 | 4.58320 | 93.2 |
| 20 | 19.594 | 4.52707 | 28.2 |
| 21 | 20.098 | 4.41467 | 5.4 |
| 22 | 20.389 | 4.35215 | 30.2 |
| 23 | 21.078 | 4.21142 | 28 |
| 24 | 21.347 | 4.15895 | 5.7 |
| 25 | 22.275 | 3.98787 | 14.5 |
| 26 | 22.492 | 3.94986 | 22 |
| 27 | 23.003 | 3.86317 | 20.5 |
| 28 | 23.383 | 3.80124 | 34.1 |
| 29 | 23.585 | 3.76920 | 38.5 |
| 30 | 24.290 | 3.66131 | 24.8 |
| 31 | 24.842 | 3.58123 | 7.3 |
| 32 | 25.184 | 3.53333 | 13.5 |
| 33 | 25.852 | 3.44352 | 10.4 |
| 34 | 26.886 | 3.31343 | 9.7 |
| 35 | 27.193 | 3.27676 | 5.2 |
| 36 | 27.675 | 3.22069 | 11.8 |
| 37 | 28.257 | 3.15570 | 13 |
| 38 | 28.613 | 3.11721 | 7.1 |
| 39 | 29.109 | 3.06524 | 8.3 |
| 40 | 29.563 | 3.01920 | 7.3 |
| 41 | 30.010 | 2.97524 | 7.1 |
| 42 | 30.901 | 2.89148 | 5 |
| 43 | 33.457 | 2.67616 | 8.1 |

The measuring conditions of the powder X-ray crystallography are the same as disclosed above.

A further object of the present invention is an improved process for preparing the 5-trityl-5,6,7,7a-tetrahydro-4H-thieno[3,2-c]pyridine-2-on of the formula (V).

A further advantage of the present process is that the converting of the Form (I) of the formula (VI) into the 5-trityl-5,6,7,7a-tetrahydro-4H-thieno[3,2-c]pyridine-2-on of the formula (V) resulted in higher yield than the known converting methods.

Preparation of the 5-trityl-5,6,7,7a-tetrahydro-4H-thieno[3,2-c]pyridine-2-on of the formula (V) was performed according to the process described in FR 2 576 901 B1 with some modifications, which resulted an environmental friendly process with better yield.

According to FR 2 576 901 B1 during the working up of the reaction mixture containing hydrogen peroxide, water is added to the reaction mixture, and it is extracted with dichloro methane. The thus obtained dichloro methane-tetrahydrofurane solvent is evaporated with vacuo. The residual product is an oil, from which the solid final product is obtained with diisopropyl ether. The yield is 64%.

During the process of the present invention the amount and ratio of the THF (which is used as the reaction medium) and water (which is added to THF during the reaction) is modified in such way that the separation of the two phases is possible, therefore there is no need to further extraction with dichloro methane or any other organic solvents. The crystalline Form I of the formula (VI) which has high melting point is used as an intermediate compound, thus a crystalline product is obtained by evaporation of the organic phase, which can be filtered form organic solvents (e.g. acetonitrile, toluene, hexane, heptane, petroleether etc.), preferably n-heptane. The yield of the 5-trityl-5,6,7,7a-tetrahydro-4H-thieno[3,2-c]pyridine-2-on of the formula (V) is 92%.

A further object of the present invention is an improved process for preparing the 5,6,7,7a-tetrahydro-4H-thieno[3,2-c]pyridine-2-on of the formula (II).

According to the process disclosed in U.S. Pat. No. 5,874,581 B1 the trityl protecting group is removed from the 5-trityl-5,6,7,7a-tetrahydro-4H-thieno[3,2-c]pyridine-2-on of the formula (V) with an equimolar amount of p-toluenesulfonic acid in a solvent containing THF, stirring the reaction mixture for 2 hours at 50° C. The process yields 93% of 5,6,7,7a-tetrahydro-4H-thieno[3,2-c]pyridine-2-on p-toluenesulfonate of the formula (II), wherein HA=PTSA.

During the improved process of the present invention the reaction can be performed at room temperature for 2 hours. This economical process variant does not require heating. The yield is 96%.

According to another process variant of the present invention, the 5,6,7,7a-tetrahydro-4H-thieno[3,2-c]pyridine-2-on of the formula (II) is produced in a simple and economical way. By the synthesis of the 5-trityl-5,6,7,7a-tetrahydro-4H-thieno[3,2-c]pyridine-2-on of the formula (V) the crystalline intermediate compound of the formula (V) is not isolated from the separated organic phase (THF). The THF solution is directly used for preparation of the 5,6,7,7a-tetrahydro-4H-thieno[3,2-c]pyridine-2-on p-toluenesulfonate of the formula (II) in the next synthetic step. The quality and the yield of the thus obtained intermediate compound of the formula (II) [calculated on the 5-trityl-4,5,6,7-tetrahydro-thieno[3,2-c]pyridine of the formula (VI)] is the same as the quality and yield of the intermediate compound of the formula (II) obtained from crystalline 5-trityl-5,6,7,7a-tetrahydro-4H-thieno[3,2-c]pyridine-2-on of the formula (V).

A further object of the present invention is an improved process for preparing the 2-acetoxi-5-(2-fluor-α-cyclopropyl-carbonyl-benzyl)-4,5,6,7-tetrahydro-4H-thieno[3,2-c]pyridine (prasugrel) of the formula (I) starting form the novel Form I of the 5-trityl-4,5,6,7-tetrahydro-thieno[3,2-c]pyridine of the formula (VI) or using thereof as an intermediate compound.

The known processes describe two-step processes for preparing the prasugrel of the formula (I) from the 5,6,7,7a-tetrahydro-4H-thieno[3,2-c]pyridine-2-on p-toluenesulfonate of the formula (II), wherein the 5-[2-cyclopropyl-1-(2-fluorphenyl)-2-oxoethyl]-5,6,7,7a-tetrahydro-4H-thieno[3,2-c]pyridine-2-on intermediate compound of the formula (IV) is prepared. The known processes use two different bases at the two steps. Most of the processes use the inflammable sodium hydride by the acylation.

The advantage of the process of the present invention is that it can be safely scaled up by replacing the sodium hydroxide by any other organic solvent. It has been surprisingly found that the two steps can be performed in the same organic solvent (DMF) and in the presence of the same organic base, in spite the fact that the organic bases used are significantly weaker bases than sodium hydroxide. Any tertiary amines (e.g triethylamine, N,N-diisopropyl-ethylamine, pyridine etc.) can be preferably used as base instead of the previously used potassium carbonate and hydrogen carbonate (by the linking reaction), and sodium hydride (by acetylation).

The reaction mixture is divided between a water-immiscible organic solvent and water and after obtaining from the organic phase, the product is prepared as a crystalline compound. The final product is purified by recrystallizing form organic an solvent, without using column chromatography.

According to the process of the present invention the 5,6,7,7a-tetrahydro-4H-thieno[3,2-c]pyridine-2-on p-toluene-sulfonate (HA=PTSA) of the formula (II) and the 2-bromo-1-cyclopropyl-2-(2-fluorphenyl)-ethanon of the formula (III) are stirred in an organic solvent, (preferably in DMF, THF, toluene, acetonitrile) by adding 1-3 mole equivalent, preferably 2-2.5 mole equivalents of amine, at 20-50° C., preferably 20-30° C., for 1-3, preferably 1-2 hours. The reaction mixture is then divided between water and ethyl acetate and the organic phase is dried and evaporated. The residual product is dissolved in an organic solvent (preferably in DMF, THF, toluene, acetonitrile) without isolating the crystalline 5-[2-cyclopropyl-1-(2-fluorphenyl)-2-oxoethyl]-5,6,7,7a-tetrahydro-4H-thieno[3,2-c]pyridine-2-on of the formula (IV). Then 1-2 equivalent, preferably 1-1.5 equivalent of an amine and 1-3 equivalent, preferably 1-2 equivalent of acetic acid anhydride is added to the reaction mixture and it is further stirred at 20-50° C., preferably 20-30° C., for 1-3 hours, preferably 1-2 hours. The reaction mixture is then divided between water and ethylacetate and the organic phase is dried and evaporated. The remaining product is recrystallized from a suitable organic solvent (acetonitrile, diisopropylether, ethanol), from the mixture of an organic solvent and water or from mixture of suitable organic solvents (toluene-ethyl acetate, hexane-ethyl acetate).

The process of the present invention provides prasugrel with a yield 38.2% of the formula (I) calculated on the starting compound of the formula (VII) and 46% calculated on the intermediate compound of the formula (II). These results show that the process of the present invention is significantly more producible than the known processes. The process of the present invention is simply applicable on industrial scale and does not require special or extreme (reaction)conditions and apparatus. During the process of the present invention there is no need to apply low temperatures (−78° C.), to use environmental unfriendly, poisonous, highly corrosive compounds, or high amounts of solvents or any technologies difficult for scale-up can avoided (such as column chromatography).

The invention is further elucidated by means of following Examples without limiting the scope of protection to the Examples.

EXAMPLES

Example 1

Preparation of the crystalline Form I
5-trityl-4,5,6,7-tetrahydro-thieno[3,2-c]pyridine of the formula (VI)

Process A:
530 cm³ of acetonitrile and 108.0 cm³ (81.8 g; 0.63 mol) of N,N-diisopropyl-ethylamine is added to 52.7 g (0.30 mole) of 4,5,6,7-tetrahydro-thieno[3,2-c]pyridine hydrochloride (VII). While stirring, 87.0 g (0.312 mole) of trityl-chloride are added to the suspension. The mixture is stirred for 3 hours and the precipitated crystals are filtered. The thus obtained intermediate compound can be used in the further synthetic steps without any further purification.

Yield: 108.0 g (94%) colorless, crystalline product
Mp.: 169-170° C., Form I characterized by powder diffraction patter shown in FIG. 1.

IR (KBr, cm⁻¹): 3425, 3055, 2828, 1595, 1487, 1447, 710.
$^1$H-NMR (DMSO-$d_6$, 500 MHz): 7.46 (6H, m); 7.31 (6H, m); 7.21 1H, d, J=5.0 Hz); 7.18 (3H, m); 6.72 (1H, d, J=5.0 Hz); 3.28 (2H, s), 2.94 (2H, m); 2.45 (2H, m).
$^{13}$C-NMR (DMSO-$d_6$, 125 MHz): 142.3; 134.6; 132.9; 128.9; 127.8; 126.3; 125.8; 123.0; 76.8; 47.5; 46.7; 25.9.

Elementary analysis [calculated on the basis of the Formula $C_{26}H_{23}NS$ (M: 381.54)]
Calculated: C, 81.85; H, 6.08; N, 3.67; S, 8.40.
Measured: C, 81.64; H, 6.19; N, 3.65; S, 8.31.

Process B:
530 cm³ of DMF and 108.0 cm³ (81.8 g; 0.63 mol) of N,N-diisopropyl-ethylamin are added to 52.7 g (0.30 mol) of 4,5,6,7-tetrahydro-thieno[3,2-c]pyridine hydrochloride (VII). While stirring, 87.0 g (0.312 mole) of trityl-chloride are added to the suspension The mixture is stirred for 4 hours and the precipitated crystals are filtered with DMF and washed with water. The thus obtained intermediate compound can be used in the further synthetic steps without any further purification.

Yield: 96.5 g (84%) colorless, crystalline product
Op.: 167-170° C., Form I characterized by powder diffraction patter shown in FIG. 1.

Example 2

Preparation of the crystalline Form II of
5-trityl-4,5,6,7-tetrahydro-thieno[3,2-c]pyridine of the formula (VI)

23 cm³ (0.083 mol) of triethyl-amine are added to the solution of 23 cm³ of dichloro methane and 11.5 g (0.083 mol) 4,5,6,7-tetrahydro-thieno[3,2-c]pyridine dropwise at room temperature and 23 g (0.083 mol) of trityl-chloride are further added to the mixture. The reaction mixture is kept at room temperature for one night and poured onto 2000 ml of water. The organic phase is separated, dried with sodium sulfate and evaporated. The colorless, paste-like crystals are dried in vacuo for 5 hours at 80° C. under 140 mbar pressure.

Yield: 28.5 g (91%) colorless, crystalline product.
Mp.: 147-152° C., Form II characterized by powder diffraction patter shown in FIG. 3.

Example 3

Preparation of 5-trityl-5,6,7,7a-tetrahydro-4H-thieno [3,2-c]pyridine-2-on of the formula (V)

750 cm³ of tetrahydrofurane are added to 95.3 g (0.25 mol) of 5-trityl-4,5,6,7-tetrahydro-thieno[3,2-c]pyridine (VI). The solution is cooled to −40° C. and 150 cm³ (0.375 mol) 2.5 M of hexane-butyl-lithium solution are added dropwise at this temperature under argon. The solution is then warmed to +10° C. and stirred for 30 minutes at this temperature. The solution is then cooled to −40° C. and the solution of 86.2 cm³ (0.375 mole) triisopropyl-borate and 200 cm³ THF is dripped in. The solution is then warmed again to +10° C. and stirred for 1 hour at this temperature. The solution is then cooled again to −40° C. and 53.75 cm³ 35 w/w % hydrogen-peroxide solution are slowly added dropwise. The temperature of the solution is allowed to warm up slowly to room temperature and the solution is stirred for 1 hour at this temperature.

300 cm³ of water are added to the solution while stirring and cooling. The phases are separated and the organic phase dried on $MgSO_4$ and is evaporated in vacuo. The residual solid product is mixed with heptane. The precipitated crystals are filtered and washed with hexane. The thus obtained product can be used in the further synthetic steps without any further purification.

Yield: 91.4 g (92%) colorless, crystalline product.
Mp.: 194-200° C.
IR (KBr, cm$^{-1}$): 3442, 3054, 2823, 1681, 1488, 1447, 1096.
$^1$H-NMR (DMSO-d$_6$, 500 MHz): 7.46 (6H, m); 7.30 (6H, m); 7.19 (3H, m); 6.07 (1H, s); 4.13 (1H, dd, J=12.1; 2.8 Hz); 3.98 (1H, dd, J=12.1; 6.3 Hz);), 3.34 (1H, dd, J=12.2; 3.2 Hz); 2.40 (1H, m); 2.18 (1H, d, J=12.1 Hz); 2.10 (1H, dd, J=12.2; 3.8 Hz); 1.68 (1H, dt, J=12.1; 1.8 Hz).
$^{13}$C-NMR (DMSO-d$_6$, 125 MHz): 199.1; 169.8; 129.0; 127.8; 126.5; 125.7; 77.5; 51.6; 50.7; 47.6; 35.2.

Elementary analysis [calculated on the basis of the formula of C$_{26}$H$_{23}$NOS (M: 397.54)]
Calculated: C, 78.55; H, 5.83; N, 3.52; S, 8.07.
Measured: C, 78.15; H, 5.50; N, 3.31; S, 7.70.

Example 4

Preparation of 5,6,7,7a-tetrahydro-4H-thieno[3,2-c]-pyridine-2-on toluene-4-sulfonate of the formula II (HA=PTSA)

Process A:
1300 cm$^3$ of tetrahydrofurane are added to 86.7 g (0.218 mole) of 5-trityl-5,6,7,7a-tetrahydro-4H-thieno[3,2-c]pyridine-2-on (V) and 41.5 g (0.218 mol) of toluene-4-sulfonate-monohydrate are further added under intensive stirring. The reaction mixture is stirred for 2 hours at room temperature. The reaction mixture is cooled in an ice water bath to 0-5° C., stirred for 3-4 hours, filtered and washed with tetrahydrofurane. The thus obtained product can be used in the further synthetic steps without any further purification.

Yield: 68.2 g (96%) colorless, crystalline product.
Mp.: 198-200° C.
IR (KBr, cm$^{-1}$): 3441, 3015, 2827, 1697, 1591, 1446, 1203, 1164, 1123, 1032, 1008.
$^1$H-NMR (DMSO-d$_6$, 500 MHz): 9.30 (1H, bs); 8.98 (1H, bs); 7.53 (2H, d, J=8.1 Hz); 7.14 (2H, d, J=8.1 Hz); 6.45 (1H, t, J=1.5 Hz); 4.74 (1H, dd, J=12.1; 5.3 Hz); 4.40 (1H, d, J=13.9 Hz); 4.01 (1H, d, J=13.7 Hz); 3.46 (1H, d, J=11.5 Hz); 3.28 (1H, t, J=13.0 Hz); 2.59 (1H, m); 2.39 (3H, s); 1.88 (1H, m).
$^{13}$C-NMR (DMSO-d$_6$, 125 MHz): 197.4; 163.9; 144.9; 138.5; 129.3; 128.5; 125.6; 47.7; 44.0; 42.6; 30.8; 21.0.

Elementary analysis [calculated on the basis of the formula of C$_{14}$H$_{17}$NO$_4$S$_2$ (M: 327.42)]
Calculated: C, 51.36; H, 5.23; N, 4.28; S, 19.59.
Measured: C, 51.17; H, 5.25; N, 4.13; S, 19.63.

Process B:
750 cm$^3$ of tetrahydrofurane are added to 95.3 g (0.25 mol) of 5-trityl-4,5,6,7-tetrahydro-thieno[3,2-c]pyridine (VI). The solution is cooled to −40° C. and 150 cm$^3$ (0.375 mol) 2.5 M of hexane-butyl-lithium solution are added dropwise at this temperature under argon. The solution is then warmed to +10° C. and stirred for 30 minutes at this temperature. The solution is then cooled to −40° C. and the solution of 86.2 cm$^3$ (0.375 mole) of triisopropyl-borate and 200 cm$^3$ of THF are added dropwise. The solution is then warmed again to +10° C. and stirred for 1 hour at this temperature. The solution is then cooled again to −40° C. and 53.75 cm$^3$ 35 w/w % of hydrogen-peroxide solution are slowly added dropwise. The temperature of the solution is allowed to warm up slowly to room temperature and the solution is stirred for 1 hour at this temperature.

300 cm$^3$ of water are added to the solution while stirring and cooling. The phases are separated and the organic layer is dried on MgSO$_4$ and 47.5 g (0.25 mol) of toluene-4-sulfonate-monohydrate are added under intensive stirring. The reaction mixture is stirred at room temperature for 2 hours. The reaction mixture is cooled by an ice water bath to 0-5° C., stirred for 3-4 hours, filtered and washed with tetrahydrofurane. The thus obtained product can be used in the further synthetic steps without any further purification.

Yield: 73.8 g (90%) colorless, crystalline product.
Mp.: 198-200° C.

Example 5

Preparation of 2-Acetoxi-5-(2-fluor-α-cyclopropyl-carbonyl-benzyl)-4,5,6,7-tetrahydro-4H-thieno[3,2-c]pyridine (prasugrel, I)

1$^{st}$ step:
150 cm$^3$ of DMF are added to 65.5 g (0.2 mol) of 5,6,7,7a-tetrahydro-4H-thieno[3,2-c]-pyridine-2-on para-toluene-sulfonate (II, HA=PTSA). 75.3 cm$^3$ (56.9 g; 0.44 mol) of N,N-diisopropyl-ethyl-amine (DIPEA) are added to the solution and 55.4 g of 2-bromo-1-cyclopropyl-2-(2-fluorophenyl)-ethanon (III) (containing 92.8% of GC) dissolved in 94 cm$^3$ (88.7 g) of dimethyl-formamide are added dropwise within app. 30 minutes under ice water cooling. The mixture is stirred for 1 hour at room temperature. The reaction mixture is poured onto the mixture of ice water and ethyl acetate. The phases are separated and the aqueous phase is extracted with ethyl acetate. The collected organic phases are dried on MgSO$_4$. The solvent is removed in vacuo.

2$^{nd}$ step:
28.4 cm$^3$ (30.6 g; 0.30 mole) of acetic anhydride are added dropwise to the mixture of 70 ml of DMF and 37.65 cm$^3$ (28.43 g; 0.22 mole) of DIPEA at 15-20° C. under intensive stirring. The solution of the residual product of the step 1 and 120 ml of DMF are added dropwise to the reaction mixture under intensive stirring at 20-25° C. The mixture is stirred for 1 hour at room temperature. The reaction mixture is poured onto the mixture of ice water and ethyl acetate. The phases are separated and the aqueous phase is extracted with ethyl acetate. The collected organic phases are dried on MgSO$_4$. The solvent is removed in vacuo and ethanol is added to the residual product. After cooling to 0-5° C. the precipitated crystals are filtered, washed with ethanol. The yield is 38.1 g (51%) crude prasugrel base. The crude product is recrystallized form acetonitrile.

Yield: 34.4 g (46.0%) colorless, crystalline product
Yield for the whole synthetic process, calculated on the 4,5,6,7-tetrahydro-thieno[3,2-c]pyridine hydrochloride of the formula (VII) is 38.2%.
Mp.: 120-121° C.
IR (KBr, cm$^{-1}$): 3388, 2920, 2767, 1758, 1704, 1586, 1488, 1369, 1217, 1194, 1127, 1011.
$^1$H-NMR (CDCl$_3$, 500 MHz): 7.47 (1H, td, J=7.5; 1.8 Hz); 7.30 (1H, m); 7.16 (1H, td, J=7.5; 1.1 Hz); 7.10 (1H, td, J=8.2; 1.1 Hz); 6.26 (1H, s); 4.82 (1H, s); 3.56 (1H, d, J=14.3 Hz); 3.48 (1H, d, J=14.3 Hz); 2.90 (1H, m); 2.78 (3H, m); 2.28 (1H, m); 2.23 (3H, s); 1.05 (1H, m); 1.00 (1H, m); 0.84 (2H, m).
$^{13}$C-NMR (CDCl$_3$, 125 MHz): 207.4; 167.5; 161.1; 149.4; 130.4; 129.7; 129.3; 125.6; 124.2; 122.0; 115.6; 112.8; 71.5; 50.3; 48.3; 24.9; 20.4; 18.1; 11.8; 11.3.

Elementary analysis [calculated on the basis of the formula of C$_{20}$H$_{20}$FNO$_3$S (M: 373,45)]
Calculated: C, 64.33; H, 5.40; N, 3.75; S, 8.59.
Measured: C, 64.18; H, 5.50; N, 3.69; S, 8.75.

REFERENCE EXAMPLE 1

Preparation of
5-trityl-4,5,6,7-tetrahydro-thieno[3,2-c]pyridine (VI)
according to the example 1 of the U.S. Pat. No.
4,740,510

20 cm$^3$ (0.079 mole) of triethyl amine are added dropwise to the solution of 10 g (0.072 mole) of 4,5,6,7-tetrahydro-thieno[3,2-c]pyridine and 20 cm$^3$ of dichloro methane at room temperature and 20.02 g (0.072 mole) of triphenyl-methyl-chloride are added. The reaction mixture is kept at room temperature for a night and is poured onto 200 cm$^3$ of water. The phases are separated; the organic phase is dried on sodium sulfate and evaporated to dryness. The residual product is purified by silica gel chromatography using dichloro methane as eluent.

Figure 2:
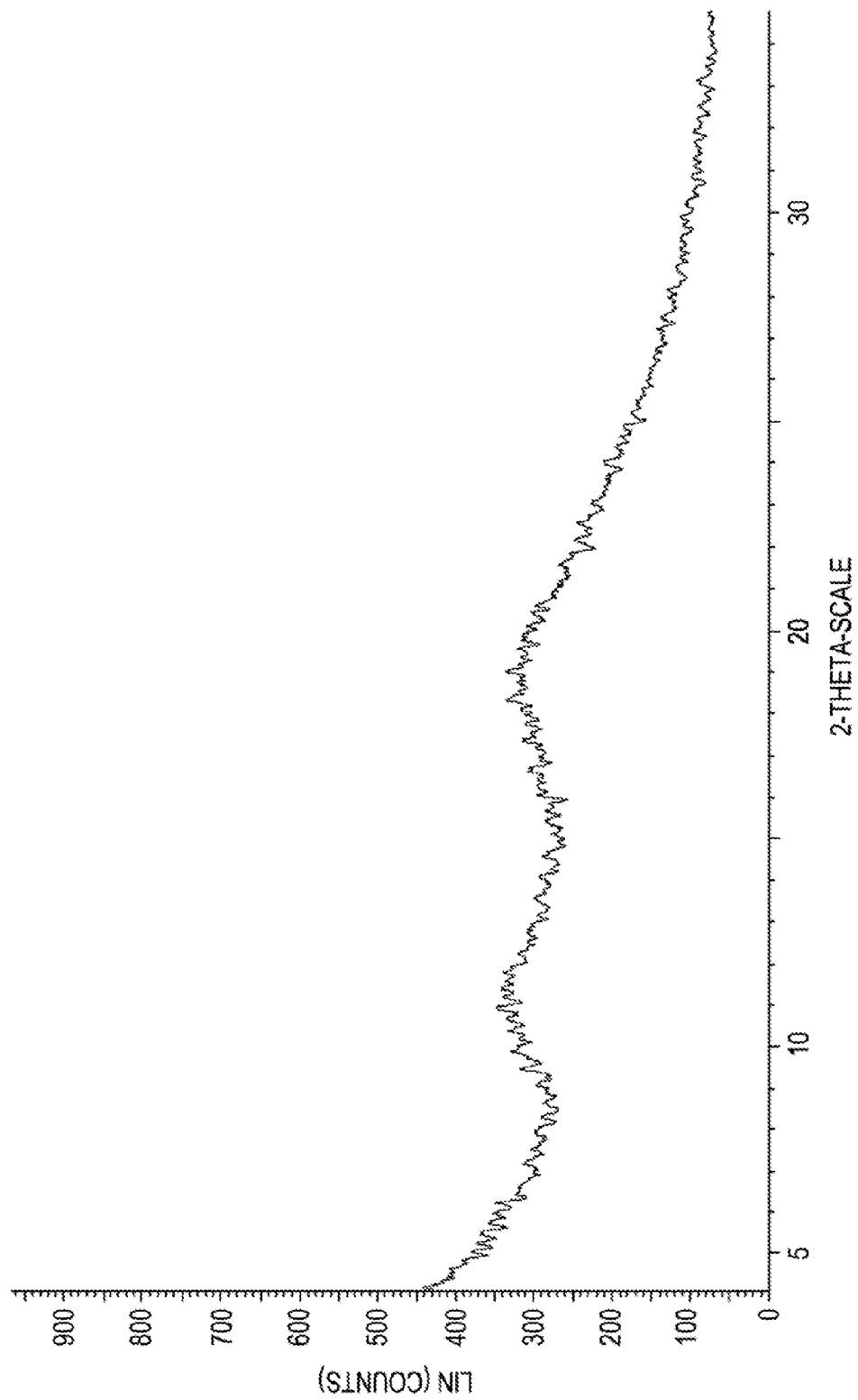
FIG. 2 depicts the X-ray powder diffraction pattern of the amorphous 5-trityl-4,5,6,7-tetrahydro-thieno[3,2-c]pyridine of the formula (VI).
Figure 3:
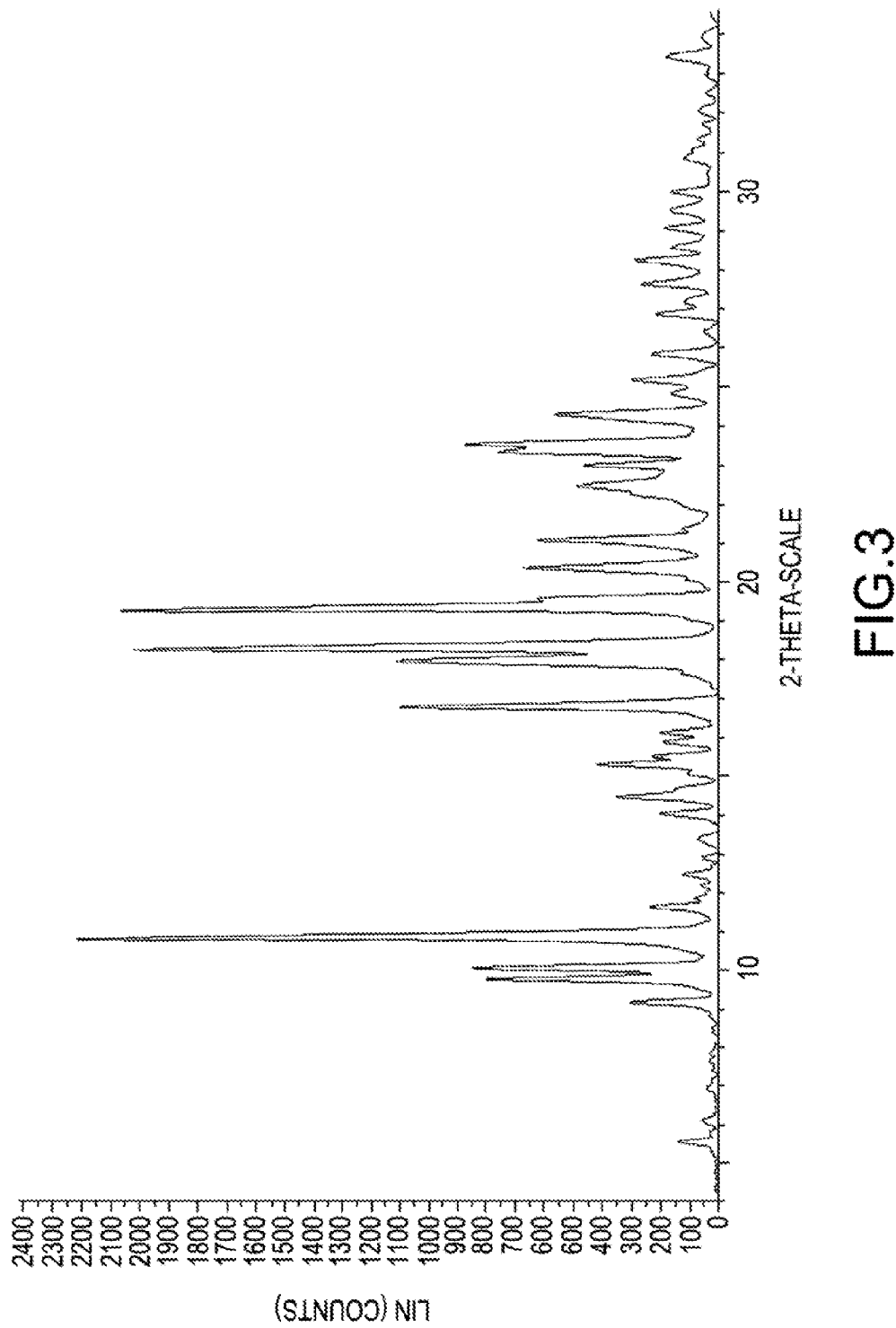
FIG. 3 depicts the X-ray powder diffraction pattern of Form II of 5-trityl-4,5,6,7-tetrahydro-thieno [3,2-c]pyridine of the formula (VI).

Yield: 28.9 g (96%) amorphous, the X-ray diffraction pattern is shown in FIG. 2.

Mp.: 92-97° C., colorless, paste-like.

$^1$H-NMR (CDCl$_3$) 7-57-6.90 (15H, m); 6.80 (1H, d, J=6.5 Hz); 6.43 (1H, d, J=6.5 Hz); 3.35 (2H, s); 3.00-2.33 (4H, m).

The invention claimed is:

1. Form I of 5-trityl-4,5,6,7-tetrahydro-thieno[3,2-c]pyridine of the formula (VI) which shows an X-ray powder diffraction pattern having characteristic peaks at reflection angle 2Θ(±0.2° 2Θ) of about 10,236; 11,938; 17,929; 19,527; 24,427.

2. Form I of 5-trityl-4,5,6,7-tetrahydro-thieno[3,2-c]pyridine of the formula (VI), which shows an X-ray powder diffraction pattern according to the following table:

| (relative intensity >5%) | | | |
|---|---|---|---|
| Peak No. | Angle 2-Theta ° | d value Angstrom | Intensity % |
| 1 | 5.790 | 15.25071 | 39.1 |
| 2 | 5.986 | 14.75396 | 16.2 |
| 3 | 10.236 | 8.63495 | 62.5 |
| 4 | 10.594 | 8.34411 | 39 |
| 5 | 11.553 | 7.65334 | 40.5 |
| 6 | 11.938 | 7.40748 | 48.7 |
| 7 | 12.718 | 6.95478 | 15.7 |
| 8 | 13.336 | 6.63384 | 30.2 |
| 9 | 13.543 | 6.53296 | 20.6 |
| 10 | 14.308 | 6.18523 | 6.1 |
| 11 | 14.685 | 6.02737 | 18.5 |
| 12 | 15.357 | 5.76519 | 10.8 |
| 13 | 15.555 | 5.69199 | 14.5 |
| 14 | 16.139 | 5.48733 | 7.1 |
| 15 | 17.929 | 4.94340 | 100 |
| 16 | 18.259 | 4.85488 | 16 |
| 17 | 18.598 | 4.76707 | 7 |
| 18 | 19.052 | 4.65440 | 13 |
| 19 | 19.527 | 4.54244 | 79.8 |
| 20 | 20.032 | 4.42890 | 16.9 |
| 21 | 20.254 | 4.38092 | 18.9 |
| 22 | 20.536 | 4.32133 | 30.4 |
| 23 | 20.853 | 4.25637 | 21.8 |
| 24 | 21.525 | 4.12511 | 29.1 |
| 25 | 21.907 | 4.05403 | 9.1 |
| 26 | 22.343 | 3.97587 | 22.8 |
| 27 | 22.894 | 3.88134 | 6.4 |
| 28 | 23.240 | 3.82430 | 11.9 |
| 29 | 23.593 | 3.76788 | 23.7 |
| 30 | 23.903 | 3.71978 | 21.7 |
| 31 | 24.427 | 3.64109 | 58.6 |
| 32 | 25.575 | 3.48021 | 6.2 |
| 33 | 27.268 | 3.26790 | 9.1 |
| 34 | 27.590 | 3.23049 | 6.6 |
| 35 | 27.791 | 3.20752 | 5.9 |
| 36 | 28.809 | 3.09645 | 10.8 |
| 37 | 29.107 | 3.06544 | 7.1 |
| 38 | 30.996 | 2.88284 | 5.9 |
| 39 | 33.051 | 2.70808 | 4.7. |

3. Process for preparing the Form I of 5-trityl-4,5,6,7-tetrahydro-thieno[3,2-c]pyridine of the formula (VI) according to claim 1, wherein the 4,5,6,7-tetrahydro-thieno[3,2-c]pyridine hydrochloride salt of the formula (VII) is reacted with trityl chloride without isolation of the corresponding base of the formula (VII), in the presence of a base using an organic solvent from which the crystalline product precipitates without precipitation of the salt of the base used as acid binder.

4. Process according to claim 3, wherein organic base is used as acid binder.

5. Process according to claim 4, wherein the organic base is a tertiary amine, triethylamine or nitrogen containing heterocyclic compound.

6. Process according to claim 3, wherein the organic solvent is an aromatic hydrocarbon, an ether-type solvent, an acidamide-type solvent, a nitrile-type solvent, or a ketone-type solvent.

7. Process for preparing the compound according to claim 3, wherein the crystalline 5-trityl-4,5,6,7-tetrahydro-thieno[3,2-c]pyridine of the formula (VI starting compound is converted to the 5,6,7,7a-tetrahydro-4H-thieno[3,2-c]pyridine-2-on para-toluenesulfonate of the formula (II) without isolating the 5-trityl-5,6,7,7a-tetrahydro-4H-thieno[3,2-c]pyridine-2-on of the formula (V).

8. Process for preparing the Form I of 5-trityl-4,5,6,7-tetrahydro-thieno[3,2-c]pyridine of the formula (VI) according to claim 2, wherein the salt of the formula (VII) is reacted with trityl chloride without isolation of the corresponding base of the formula (VII), in the presence of a base using an organic solvent from which the crystalline product precipitates without precipitation of the salt of the base used as acid binder.

9. Process according to claim 8, wherein organic base is used as acid binder.

10. Process according to claim 9, wherein the organic base is a tertiary amine, triethylamine or nitrogen containing heterocyclic compound.

11. Process according to claim 8, wherein the organic solvent is an aromatic hydrocarbon, an ether-type solvent, an acidamide-type solvent, a nitrile-type solvent, or a ketone-type solvent.

12. Process for preparing 2-acetoxy-5-(2-fluoro-α-cyclopropyl-carbonyl-benzyl)-4,5,6,7-tetrahydro-4H-thieno[3,2-c]pyridine (prasugrel) of the formula (I) comprising:
converting the crystalline Form I of 5-trityl-4,5,6,7-tetrahydro-thieno[3,2-c]pyridine of the formula (VI) according to claim 1 to prasugrel.

13. Process for preparing 2-acetoxy-5-(2-fluoro-α-cyclopropyl-carbonyl-benzyl)-4,5,6,7-tetrahydro-4H-thieno[3,2-c]pyridine (prasugrel) of the formula (I) comprising:
converting the crystalline Form I of 5-trityl-4,5,6,7-tetrahydro-thieno[3,2-c]pyridine of the formula (VI) according to claim 1 to the 5,6,7,7a-tetrahydro-4H-thieno[3,2-c]pyridine-2-on para-toluenesulfonate of the formula (II), wherein HA=PTSA and further converting the compound of the formula (II) to the prasugrel of the formula (I).

14. Process for preparing 2-acetoxy-5-(2-fluoro-α-cyclopropyl-carbonyl-benzyl)-4,5,6,7-tetrahydro-4H-thieno[3,2-c]pyridine (prasugrel) of the formula (I) comprising:
converting the crystalline Form I of 5-trityl-4,5,6,7-tetrahydro-thieno[3,2-c]pyridine of the formula (VI) according to claim 1 to the 5,6,7,7a-tetrahydro-4H-thieno[3,2-c]pyridine-2-on para-toluenesulfonate of the formula (II) without preparing the 5-trityl-5,6,7,7a-tetrahydro-4H-thieno[3,2-c]pyridine-2-on of the formula (V) and further converting the compound of the formula (II) to the prasugrel of the formula (I).

15. Process according to claim 5, wherein the organic base is N,N-diisopropyl-ethylamine, triethylamine, or nitrogen containing heterocyclic compound.

16. Process according to claim 15, wherein the nitrogen containing heterocyclic compound is pyridine.

17. Process according to claim 6, wherein the organic solvent is toluene, tetrahydrofuran, dioxane, methyl tert-butyl ether, N,N-dimethylformamide, N,N-dimethylacetamide, N-methyl-pyrrolidone, acetonitrile or methyl-ethylketone.

18. Process according to claim 10, wherein the organic base is N,N-diisopropyl-ethylamine, triethylamine, or nitrogen containing heterocyclic compound.

19. Process according to claim 18, wherein the nitrogen containing heterocyclic compound is pyridine.

20. Process according to claim 11, wherein the organic solvent is toluene, tetrahydrofuran, dioxane, methyl tert-butyl ether, N,N-dimethylformamide, N,N-dimethylacetamide, N-methyl-pyrrolidone, acetonitrile or methyl-ethylketone.

21. Process for preparing 2-acetoxy-5-(2-fluoro-α-cyclopropyl-carbonyl-benzyl)-4,5,6,7-tetrahydro-4H-thieno[3,2-c]pyridine (prasugrel) of the formula (I) comprising:
converting the 5-trityl-4,5,6,7-tetrahydro-thieno[3,2-c]pyridine of the formula (VI) according to claim 1 to the 5,6,7,7a-tetrahydro-4H-thieno[3,2-c]pyridine-2-on para-toluenesulfonate of the formula (II)

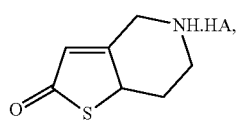

(II)

wherein HA=PTSA and further converting the compound of the formula (II) to the prasugrel of the formula (I), wherein the 4,5,6,7-tetrahydro-thieno[3,2-c]pyridine hydrochloride salt of the formula (VII)

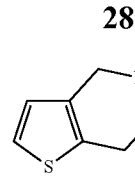

·HCl is reacted with trityl chloride without isolation of the corresponding base of the formula (VII), in the presence of a base, and using an organic solvent selected from N,N-dimethylformamide, N,N-dimethylacetamide, N-methyl-pyrrolidone or acetonitrile from which the crystalline product of the Form I shows an X-ray powder diffraction pattern having characteristic peaks at reflection angle 2Θ(±0.2° 2Θ) of about 10,236; 11,938; 17,929; 19,527; 24,427 and precipitates directly or after dilution the reaction mixture with water without precipitation of the salt of the base used as acid binder.

22. Process for preparing 2-acetoxy-5-(2-fluoro-α-cyclopropyl-carbonyl-benzyl)-4,5,6,7-tetrahydro-4H-thieno[3,2-c]pyridine (prasugrel) of the formula (I) comprising:
converting the crystalline Form I of 5-trityl-4,5,6,7-tetrahydro-thieno[3,2-c]pyridine of the formula (VI) according to claim 2 to prasugrel.

23. Process for preparing 2-acetoxy-5-(2-fluoro-α-cyclopropyl-carbonyl-benzyl)-4,5,6,7-tetrahydro-4H-thieno[3,2-c]pyridine (prasugrel) of the formula (I) comprising:
converting the crystalline Form I of 5-trityl-4,5,6,7-tetrahydro-thieno[3,2-c]pyridine of the formula (VI) according to claim 2 to the 5,6,7,7a-tetrahydro-4H-thieno[3,2-c]pyridine-2-on para-toluenesulfonate of the formula (II), wherein HA=PTSA and further converting the compound of the formula (II) to the prasugrel of the formula (I).

24. Process for preparing 2-acetoxy-5-(2-fluoro-α-cyclopropyl-carbonyl-benzyl)-4,5,6,7-tetrahydro-4H-thieno[3,2-c]pyridine (prasugrel) of the formula (I) comprising:
converting the crystalline Form I of 5-trityl-4,5,6,7-tetrahydro-thieno[3,2-c]pyridine of the formula (VI) according to claim 2 to the 5,6,7,7a-tetrahydro-4H-thieno[3,2-c]pyridine-2-on para-toluenesulfonate of the formula (II) without preparing the 5-trityl-5,6,7,7a-tetrahydro-4H-thieno[3,2-c]pyridine-2-on of the formula (V) and further converting the compound of the formula (II) to the prasugrel of the formula (I).

25. Process according to claim 21, wherein the base is an organic base.

26. Process according to claim 25, wherein the organic base is a tertiary amine.

27. Process according to claim 26, wherein the tertiary amine is selected from the group consisting of N,N-diisopropyl-ethylamine, trimethylamine and nitrogen containing heterocyclic compound.

28. Process according to claim 27, wherein the nitrogen containing heterocyclic compound is pyridine.

* * * * *